(12) United States Patent
Nakayama et al.

(10) Patent No.: US 6,737,538 B2
(45) Date of Patent: May 18, 2004

(54) PURIFICATION OF SILICONE OIL

(75) Inventors: Hiroshi Nakayama, Annaka (JP);
Masao Maruyama, Annaka (JP);
Hiromi Nakabayashi, Annaka (JP);
Susumu Ueno, Takefu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/436,085

(22) Filed: May 13, 2003

(65) Prior Publication Data

US 2003/0212286 A1 Nov. 13, 2003

(30) Foreign Application Priority Data

May 13, 2002 (JP) ........................................ 2002-136694

(51) Int. Cl.$^7$ .................................................... C07F 7/08
(52) U.S. Cl. ........................ 556/450; 556/453; 556/456; 556/466
(58) Field of Search ................................ 556/450, 453, 556/456, 466

(56) References Cited

U.S. PATENT DOCUMENTS

| 3,849,332 A | * 11/1974 | Bailey et al. ................ 502/423 |
| 4,661,612 A | 4/1987 | George et al. |
| 5,684,125 A | 11/1997 | Nooren |
| 6,299,771 B1 | 10/2001 | Shmidt et al. |

FOREIGN PATENT DOCUMENTS

| DE | 34 41 353 A1 | 5/1986 |
| JP | 56-168824 A | 12/1981 |
| JP | 4-267872 A | 9/1992 |
| JP | 6-128816 A | 5/1994 |
| JP | 8-12602 A | 1/1996 |
| JP | 09 150002 A | 6/1997 |
| JP | 10-120402 A | 5/1998 |

* cited by examiner

*Primary Examiner*—Samuel Barts
(74) *Attorney, Agent, or Firm*—Birch, Stewart, Kolasch & Birch, LLP

(57) ABSTRACT

An unpurified silicone oil is treated with fibrous activated carbon, yielding a silicone oil of high purity, which will find use in the electric and electronic industry and as cosmetics.

3 Claims, No Drawings

PURIFICATION OF SILICONE OIL

This nonprovisional application claims priority under 35 U.S.C. §119(a) on Patent Application No(s). 2002-136694 filed in Japan on May 13, 2002, which is (are) herein incorporated by reference.

This invention relates to the purification of silicone oil, and more particularly, to a method for purifying silicone oil to a high level of purity to use in the electric and electronic industry and cosmetic applications.

BACKGROUND OF THE INVENTION

Silicone oil is a family of organosilicon compounds comprising straight chains or straight and branched chains of siloxane bonds, modified with organic groups attached to silicon atoms as typified by methyl and phenyl groups. The viscosity of silicone oil varies over a wide range of 0.65 to 1,000,000 centistokes (cs) at 25° C. By virtue of superior heat resistance, freeze resistance, temperature properties of viscosity, and biological action as compared with mineral oils and oils of organic origins such as animal and plant oils, the silicone oil has already been widely used in the industry.

As silicone oil has found increasing novel applications for recent decades, oils produced by prior art methods do not necessarily possess all satisfactory properties. To acquire appropriate properties for a particular application, novel production methods or purification methods have been developed. Through further modifications made thereon, industrial methods have been established.

Nevertheless, in the electric and electronic industry and cosmetic application, especially in recent years, it is a matter of great urgency to obtain a silicone oil of high purity with a minimal impurity content.

Meanwhile, the raw material from which silicone oil is produced is composed mainly of dimethyldichlorosilane which is a monomer isolated to a high degree by distillation and optionally, a monochlorosilane (isolated by distillation) for end formation and a dichlorosilane containing phenyl or other organic groups for imparting certain properties, which are optionally hydrolyzed to form a siloxane intermediate, which is polymerized to eventually form a silicone oil. Almost for a certainty, the assistants used in this process are only a polymerization catalyst and a neutralizing agent. Therefore, the target for high purity is how to remove minor amounts of catalyst residue and by-products. At the same time, an analysis technique chosen and a preset level of these impurities dictate the level of product quality.

Prior art purification methods include neutralization, filtration, activated carbon treatment, water washing and the like, which are optionally used in combination. These methods are not necessarily satisfactory. Although impurities are basically removed by water washing, the generation of a large amount of waste water and the installation and time needed for separation become serious problems. Among the above-mentioned methods, the activated carbon method is relatively easy and effective to a certain extent, but suffers from difficulties of handling including large amounts of carbon used, the concomitant problem of waste carbon, and complete removal of activated carbon fines after the treatment. There is a need to develop a simple, inexpensive, stable method entailing a minimized amount of waste and capable of mass scale production.

SUMMARY OF THE INVENTION

An object of the present invention is to provide a method for purifying silicone oil which is simple, inexpensive and stable, entails a minimized amount of waste, and can offer a silicone oil of high purity and quality enough to find use in the electric/electronic and cosmetic applications.

Studying activated carbon, we have found that a specific activated carbon has an activity to purify silicone oil. More specifically, an attempt to treat a crude or unpurified silicone oil with fibrous activated carbon, especially activated carbon fibers based on carbon fibers derived from phenolic resins becomes a simple, inexpensive, stable purification method with minimized waste. The silicone oil obtained by this purification method has a high purity enough to find use in the electric/electronic and cosmetic applications.

Therefore, the present invention provides a method for purifying silicone oil by treating silicone oil with fibrous activated carbon.

DESCRIPTION OF THE PREFERRED EMBODIMENTS

Activated carbons include those derived from natural wood sources such as coconut shell-origin activated carbon and charcoal-origin activated carbon, and are often in powder or granular form. From the past, they have long been utilized in the organic chemistry field for purification, decoloring and removal of trace ingredients. The application of activated carbon to the electronic industry was recently reported as disclosed in JP-A 8-12602. There are also known coal-origin activated carbons, such as those derived from coal and tar. Recently, activated carbon in fibrous form is available. It is reported that a certain activated carbon exerts a specific function depending on its shape and its composition or microstructure which will be inherent to its origin, and is used in a particular application requiring such a function. See JP-A 56-168824, JP-A 4-267872, JP-A 6-128816 and JP-A 10-120402. These prior art approaches challenged to increase the level of purification to the limit of analysis, but failed to establish an industrially acceptable process. The material that the present invention addresses is silicone oil which is a family of organosilicon compounds.

Namely, the present invention is essentially different from the prior art techniques discussed above. It has been found that for the purification of silicone oil to a higher level, fibrous activated carbon is outstandingly effective. The concept of purifying silicone oil using fibrous activated carbon is based on a unique combination of a specific material with its applicable properties. The present invention is predicated on this finding.

Although the purifying ability of fibrous activated carbon is apparently regarded similar to the purifying ability of granular activated carbon commonly used in the prior art, a definite difference is seen between them when used in the purification of silicone oil. Of course, the difference is considered partially inherent to the chemical and physical properties of the original fibers, while the relationship of the exact material and properties on the activated carbon side to the object to be purified has not been well understood.

The silicone oil to be purified herein is not critical. The silicone oil which can be used herein is one obtained by using as a main component a diorganodichlorosilane such as dimethyldichlorosilane which is a monomer isolated to a high level of purity by distillation and optionally, a monochlorosilane (isolated by distillation) for end formation such as trimethylmonochlorosilane, and a dichlorosilane containing phenyl or other organic groups for imparting certain properties such as diphenyldichlorosilane or methylphenyldichlorosilane, optionally hydrolyzing the monomer or monomers to form a siloxane intermediate, and polymerizing the intermediate.

The viscosity of the silicone oil is not critical as long as it is oily. For filtration and other properties, the silicone oil should preferably have a viscosity of up to 10,000 cs, especially up to 5,000 cs at 25° C. The structure of the silicone oil is not critical as well and may be terminated with a triorganosilyl group such as trimethylsilyl or a diorganohydroxysilyl group.

Impurities which can be most effectively removed by the fibrous activated carbon include hydrocarbons and anionic impurities as typified by sulfate ions and chloride ions. Hydrocarbons can give off oily odor and incur color deficiencies. Ionic impurities can exacerbate insulating properties and high-temperature stability.

The content of impurities in the oil to be purified depends on the starting material and preparation conditions and is preferably in the range of not more than about 5,000 ppm, especially not more than 1,000 ppm of hydrocarbons and not more than about 100 ppm, especially not more than 50 ppm of ionic impurities such as sulfate ions and chloride ions.

The fibrous activated carbon used herein is not critical as long it is fibrous. Preferably, it has a diameter of 5 to 15 $\mu$m, an outer surface area of 0.1 to 2.0 m$^2$/g, and a specific surface area of 800 to 2,500 m$^2$/g. Examples of the fibrous activated carbon include those derived from rayon, pitch, acrylic resins and phenolic resins. Of these, fibrous activated carbons derived from phenolic resins are preferred. The activated carbon fibers derived from phenolic resins are available, for example, as Kynol from Nippon Kynol, Inc.

The amount of fibrous activated carbon used may be determined in accordance with the type and amount of impurities in the silicone oil to be purified and the treating time. A small amount of fibrous activated carbon as compared with granular activated carbon and powder activated carbon is effective, and even a ppm level relative to the silicone oil to be purified is fully effective. In the batchwise treatment, the preferred amount of fibrous activated carbon is at least 0.1 ppm, more preferably at least 0.5 ppm, even more preferably at least 1 ppm based on the weight of the silicone oil to be purified. The upper limit is not critical, but from an economical aspect, the amount of fibrous activated carbon is preferably up to 20 parts, more preferably up to 10 parts, even more preferably up to 5 parts by weight per 100 parts by weight of the silicone oil. In the continuous treatment, the silicone oil is preferably fed at a flow rate of 0.01 to 10,000 g/min, more preferably 0.1 to 1,000 g/min, even more preferably 0.5 to 500 g/min per gram of the fibrous activated carbon.

The method of purifying silicone oil according to the invention requires effective contact of fibrous activated carbon with the silicone oil to be purified, as in the case of granular activated carbon treatment. For example, the fibrous activated carbon is admitted into and mixed with a liquid to be purified, the flowpath of a cartridge or container is filled with the fibrous activated carbon, or the fibrous activated carbon is incorporated in a paper filter. The use of a cartridge filled with the fibrous activated carbon is practically favorable because continuous treatment is possible. For the continuous treatment through a cartridge filled with the fibrous activated carbon, the preferred treating conditions include a temperature of about 10 to 80° C., especially about 20 to 50° C. and a contact time of about 5 seconds to about 20 minutes, more preferably about 20 seconds to about 5 minutes, especially about 30 seconds to about 2 minutes.

The purified silicone oil resulting from the above treatment can be analyzed by washing the product with water to extract impurities therewith, and analyzing the extracted water by ion chromatography to detect SO$_4$ ions and Cl ions as ionic impurities originating from the catalyst. Alternatively, the overall water-soluble impurities are measured in terms of extracted water conductivity (EC) and pH, and trace metal impurities are measured by ion pair chromatography (IPC).

It is understood that the silicone oil purified by the inventive method should preferably have the content of SO$_4$ ions, Cl ions and trace metal impurities reduced to 1 ppm or lower, especially below the detection limit. Preferably, the extracted water conductivity (EC) is 1 $\mu$S/cm or lower and the pH is approximate to that of original water used in extraction.

Using fibrous activated carbon, the present invention renders the purification of silicone oil very simple and efficient, minimizes used water or wastes and improves industrial productivity. The silicone oil purified by the present invention has a high and consistent level of purification and a quality stability enough to find use in the electric and electronic field and the cosmetic application. The purified silicone oil satisfies the requirement in a novel application and allows development of a new market.

EXAMPLE

Examples of the invention are given below by way of illustration and not by way of limitation. The unpurified oil (silicone oil) used was a trimethylsilyl-terminated dimethylsilicone oil obtained through conventional equilibration polymerization in the presence of an acid catalyst.

Reference Example

Screening 1

To remove ionic impurities from a dimethylsilicone oil having a viscosity of 500 cs at 25° C., several adsorbents were tested by the following procedure.

To the unpurified oil, each adsorbent (A1 to A6) shown in Table 1 was added in an amount of 10% by weight based on the unpurified oil. The oil was shaken for 24 hours at room temperature, following which the adsorbent was removed by filtration. The treated oil was examined for extracted water properties and ease of filtration.

The extracted water properties were examined by mixing the treated oil, toluene and pure water in a ratio of 1:1:1, shaking the mixture for 1 hour at room temperature, and analyzing the water layer for pH, electrical conductivity, sulfate ion content and chloride ion content. The sulfate and chloride ion contents were measured by ion chromatography. By measuring the time taken until the silicone oil with the adsorbent added had been passed through a filter under a pressure of 0.2 MPa, the ease of filtration was evaluated in four ratings.

Excellent: less than 1 minute
Good: 1 minute to less than 15 minutes
Fair: 15 minutes to less than 60 minutes
Poor: 60 minutes or longer The results are shown in Table 1.

TABLE 1

| | | Extracted water properties | | | |
|---|---|---|---|---|---|
| | pH | Conductivity ($\mu$S/cm) | SO$_4$ ion (ppm) | Cl ion (ppm) | Ease of filtration |
| unpurified oil | 4.48 | 15.2 | 1.14 | 0.71 | |
| A1 filter paper filtration | 4.72 | 9.2 | 1.01 | 0.38 | Excellent |
| A2 zeolite | 7.09 | 12.3 | 0.63 | 0.62 | Excellent |
| A3 CaO | 10.48 | 49 | 0.46 | 0.06 | Poor |
| A4 Na$_2$CO$_3$ | 6.61 | 2.6 | 0.05> | 0.06 | Fair |
| A5 CaCO$_3$ | 5.6 | 1.0 | 0.05> | 0.05> | Poor |
| A6 granular activated carbon | 5.66 | 1> | ND | ND | Good |

*ND: not detected

It is evident from Table 1 that activated carbon is most effective for removing ionic impurities. Ps Screening 2

In screening 1, the amount of adsorbent was reduced and the test was conducted at an elevated temperature.

To the unpurified oil, each adsorbent (B1 to B5) shown in Table 2 was added in an amount of 5% by weight (B1, B3–B5) or 1% by weight (B2) based on the unpurified oil. The oil was agitated for 24 hours at 80° C., following which the adsorbent was removed by filtration. The treated oil was similarly examined for extracted water properties and ease of filtration. The results are shown in Table 2.

TABLE 2

| | pH | Conductivity ($\mu$S/cm) | $SO_4$ ion (ppm) | Cl ion (ppm) | Ease of filtration |
|---|---|---|---|---|---|
| unpurified oil | 4.48 | 15.2 | 1.14 | 0.71 | |
| B1 granular activated carbon (5 wt %) | 5.57 | 1> | ND | ND | Good |
| B2 granular activated carbon (1 wt %) | 5.53 | 1> | ND | ND | Good |
| B3 $Na_2CO_3$ (5 wt %) | 5.7 | 1> | ND | 0.05> | Fair |
| B4 $CaCO_3$ (5 wt %) | 7.25 | 24 | ND | 0.05> | Poor |
| B5 zeolite (5 wt %) | 6.12 | 2.9 | 0.3 | 0.29 | Excellent |

*ND: not detected

It is evident from Table 2 that activated carbon is most effective for removing ionic impurities.

Examples 1–7 and Comparative Examples 1–2
Activated Carbon Comparison 1

A continuous adsorption test was conducted using a cartridge with the adsorbent (C1 to C3) shown in Table 3. The cylindrical cartridge had a height of 250 mm, an outer diameter of 65 mm and an inner diameter of 30 mm. The space between the outer and inner shells was loaded with the adsorbent (activated carbon granules or fibers) in the amount shown in Table 3. The loaded amount is the permissible maximum loading of the cartridge.

Through the cartridge, the unpurified oil (dimethylsilicone oil having a viscosity of 500 cs at 25° C.) was passed at the feed rate shown in Table 3 and at room temperature. The thus treated oil was tested for extracted water properties by the same method as above.

The results are shown in Table 3.

TABLE 3

| | | | Feed rate (kg/min) | Extracted water properties | | |
|---|---|---|---|---|---|---|
| | | | | pH | Conductivity ($\mu$S/cm) | $SO_4$ ion (ppm) | Cl ion (ppm) |

| | | | Feed rate (kg/min) | pH | Conductivity ($\mu$S/cm) | $SO_4$ ion (ppm) | Cl ion (ppm) |
|---|---|---|---|---|---|---|---|
| | | unpurified oil | | 4.43 | 13.4 | 1.43 | 0.40 |
| Comparative Example 1 | C1 | granular activated carbon, 180 g | 0.32 | 4.79 | 6.0 | 0.86 | 0.14 |
| Comparative Example 2 | | | 0.99 | 4.47 | 13.1 | 1.52 | 0.15 |
| Example 1 | C2 | Cellulose base activated carbon fibers (by Toyobo Co., Ltd.), 100 g | 0.42 | 5.32 | 1.0 | 0.03 | 0.01 |
| Example 2 | | | 1.19 | 5.30 | 1.3 | 0.12 | 0.01 |
| Example 3 | | | 1.73 | 5.19 | 1.4 | 0.12 | 0.01 |
| Example 4 | C3 | phenolic resin base activated carbon fibers (Kynol), 100 g | 0.32 | 5.52 | 1> | 0.01 | 0.01 |
| Example 5 | | | 1.07 | 5.42 | 1> | 0.01 | 0.01 |
| Example 6 | | | 1.65 | 5.35 | 1> | 0.01 | 0.01 |
| Example 7 | | | 2.54 | 5.42 | 1> | 0.01 | 0.01 |

It is evident that the fibrous activated carbon exhibits a superior adsorption ability to the granular activated carbon, despite a smaller loading amount. In particular, the fibrous activated carbon derived from phenolic resin is effective for substantially completely removing impurities over the entire flow rate range.

Example 8 and Comparative Example 4
Activated Carbon Comparison 2

Different types of activated carbon were compared for their ability to remove metallic impurities.

To 100 g of the unpurified oil (dimethylsilicone oil having a viscosity of 500 cs at 25° C.) was added 1% by weight (based on the unpurified oil) of the activated carbon (D1, D2) shown in Table 4. The oil was agitated for one hour at 80° C., after which the activated carbon was separated by filtration. The contents of metals in the filtrate were determined by IPC emission analysis. The results are shown in Table 4.

TABLE 4

| | | Metals (ppm) | | | | | |
|---|---|---|---|---|---|---|---|
| | | Na | K | Ca | Mg | Al | Fe |
| | unpurified oil | 0.27 | 2.5 | 0.1 | 0.1 | 0.05 | 0.05 |
| Comparative Example 4 | D1 granular activated carbon | 0.05 | 0.05 | 0.08 | ND | 0.02 | 0.02 |
| Example 8 | D2 phenolic resin base activated carbon fibers | ND | ND | ND | ND | 0.02 | ND |

*ND: not detected

It is seen that the fibrous activated carbon has a superior adsorption ability to the granular activated carbon.

Examples 9–11 and Comparative Examples 5–7
Activated carbon comparison 3

Different types of activated carbon were compared for their adsorption ability.

To 500 g of the unpurified oil (dimethylsilicone oil having a viscosity of 500 cs at 25° C.), the activated carbon (E1, E2) shown in Table 5 was added in the concentration shown in Table 5. The oil was agitated for 24 hours at 80° C., after which the activated carbon was separated by filtration. The treated oil was analyzed for extracted water properties by the same method as above. The results are shown in Table 5.

TABLE 5

| | | | Extracted water properties | | | |
|---|---|---|---|---|---|---|
| | | | pH | Conductivity ($\mu$S/cm) | $SO_4$ ion (ppm) | Cl ion (ppm) |
| | | unpurified oil | 4.43 | 13.4 | 0.56 | 1.01 |
| Comparative Example 5 | E1 | granular activated carbon 5 ppm | 5.09 | 6.9 | 0.18 | 0.65 |
| Comparative Example 6 | | 10 ppm | 5.15 | 1> | 0.05 | 0.12 |
| Comparative Example 7 | | 20 ppm | 5.25 | 1> | 0.01 | 0.05 |
| Example 9 | E2 | phenolic resin base activated carbon fibers 2.5 ppm | 5.3 | 2.1 | 0.09 | 0.32 |
| Example 10 | | 5 ppm | 5.55 | 1> | 0.01 | 0.1 |
| Example 11 | | 10 ppm | 5.6 | 1> | 0.01 | 0.01 |

It is seen that the fibrous activated carbon has an adsorption ability which is at least twice greater than that of the granular activated carbon.

Using fibrous activated carbon, the invention enables to perform a high level of purification in a simple manner and achieves a significant reduction of wastes. There is readily obtained a highly purified silicone oil suited for new applications in the electric and electronic industry and as cosmetics.

What is claimed is:

1. A method for purifying silicone oil, comprising treating silicone oil with fibrous activated carbon.

2. The method of claim 1 wherein the fibrous activated carbon is derived from a phenolic resin.

3. The method of claim 1, comprising the steps of placing the fibrous activated carbon in a container to fill a silicone oil flowpath therewith, and passing the silicone oil through the flowpath of the container for bringing the silicone oil in contact with the fibrous activated carbon for conducting continuous treatment.

* * * * *